(12) United States Patent
Pompeo et al.

(10) Patent No.: US 7,488,702 B2
(45) Date of Patent: Feb. 10, 2009

(54) SOLVENTLESS FORMULATION OF TRICLOPYR BUTOXYETHYL ESTER

(76) Inventors: Michael P. Pompeo, 925 Windrow Ct., Sumter, SC (US) 29150; Alefesh Hailu, 6834 Perinwood Dr., Cincinnati, OH (US) 45248; Jeffrey Lee Jensen, 8906 N. County Rd. 1050 East, Brownsburg, IN (US) 46112; Patrick Littleton Burch, 3425 Elk Creek Dr., Christiansburg, VA (US) 24073; William Newton Kline, III, 2716 Saxon Dr., Duluth, GA (US) 30096; John Lawrence Troth, 11229 Lakeshore Dr. West, Carmel, IN (US) 46033

( * ) Notice: Subject to any disclaimer, the term of this patent is extended or adjusted under 35 U.S.C. 154(b) by 0 days.

(21) Appl. No.: 11/601,231

(22) Filed: Nov. 17, 2006

(65) Prior Publication Data

US 2007/0191229 A1 Aug. 16, 2007

Related U.S. Application Data

(60) Provisional application No. 60/773,417, filed on Feb. 15, 2006.

(51) Int. Cl.
*A01N 43/40* (2006.01)
*A01N 65/00* (2006.01)
(52) U.S. Cl. .................. 504/244; 504/189; 504/130
(58) Field of Classification Search .............. 504/254, 504/244, 189, 130
See application file for complete search history.

(56) References Cited

U.S. PATENT DOCUMENTS 5,466,659 A 11/1995 Keeney et al.
5,538,662 A 7/1996 Klier et al.
5,834,006 A 11/1998 Smith et al.
5,905,072 A 5/1999 Capuzzi et al.
6,017,559 A 1/2000 Mulqueen et al.
6,586,366 B1 7/2003 Auda et al.
6,586,479 B2 7/2003 Miller et al.
2003/0069135 A1* 4/2003 Kober et al. ............. 504/116.1
2004/0224844 A1* 11/2004 Bickers et al. ............. 504/111

FOREIGN PATENT DOCUMENTS

| AU | 2004100006 A4 | 3/2004 |
| WO | WO 96/28027 A1 | 9/1996 |
| WO | WO 2004/093546 A1 | 11/2004 |
| WO | WO 2007/094836 A1 | 8/2007 |

OTHER PUBLICATIONS

Forster, A., Surfactant Formulations to Enhance Triclopyr Amine Efficacy: Effects on Adhesion, Retention and Contact Phytotoxicity on Three Hardwood Species, 1998, Virginia Polytechnic Institute and State University.*
Curtis M. Elsik, et al., "Microemulsion Formulation of Agricultural Adjuvants", Proceedings of 6th International Symposium on Adjuvants for Agrochemicals, ISAA 2001, Amsterdam, The Netherlands, Editor: Hans de Ruiter, Aug. 13-17, 2001, pp. 403-408.
Tergitol™ XDLW Surfactant Technical Data Sheet.
Garlon® 4 Herbicide Material Safety Data Sheet.
Garlon® 4 Speciality Herbicide Specimen Label.
Bovey Rooney W et al: "Honey mesquite (Prosopis glandulosa) control by synergistic action of clopyralid: Triclopyr mixtures" Weed Science, vol. 40, No. 4, 1992, pp. 563-567, XP009080681.
Bebawi F F et al.: "Impact of foliar herbicides on pod and seed behavior of rust-infected rubber vine (Cryptostegia grandiflora) plants" Plant Protection Quarterly, vol. 14, No. 2, 1999, pp. 57-62, XP009080682.

* cited by examiner

*Primary Examiner*—Sreeni Padmanabhan
*Assistant Examiner*—Danielle Sullivan

(57) ABSTRACT

A solventless herbicidal composition of triclopyr butoxyethyl ester and a surfactant provides efficient control of woody plants while reducing exposure to aromatic carriers.

4 Claims, No Drawings

SOLVENTLESS FORMULATION OF TRICLOPYR BUTOXYETHYL ESTER

CROSS REFERENCE TO RELATED APPLICATIONS

This application claims priority, under 35 U.S.C. §119(e), of U.S. Provisional Patent Application No. 60/773,417, filed on Feb. 15, 2006, the entire contents of which are incorporated herein by reference.

FIELD OF THE INVENTION

This invention concerns a novel triclopy butoxyethyl ester composition.

BACKGROUND OF THE INVENTION

Today's increased attention to nature and the environment has resulted in unprecedented efforts to encourage grasses, low-growing ground cover, and wildflowers on rights-of-way. In electric utility rights-of-way, tall growing tree and shrub species interfere with electrical line maintenance operations and if left uncontrolled can result in trees growing into power lines, resulting in power outages. On roadside rights of way, tall growing weeds interfere with water drainage from the road edge, resulting in more frequent need for road maintenance, restrict ability of motorists to use the road shoulder, cause poor vision along the right-of-way and contribute to spread of untreated noxious weed species into adjacent crop lands. In forest lands, removal of unwanted tall growing trees and woody shrubs is a frequent forest management practice in order to encourage growth of desirable tree species. Thus control treatments are required to remove tall-growing woody plants in vegetation control programs. Not only do such treatment programs result in effective, long lasting brush control, they leave non-target plants virtually untouched. This allows desired plants to thrive because they are freed from competition for moisture, nutrients and sunlight.

One such treatment program consists of the use of basal bark or stem application of an herbicide to control undesired vegetation. This particular method is attractive because it provides not only vegetation control but also efficient placement and utilization of the herbicide composition on individual plants. U.S. Pat. No. 5,466,659 describes this method of treatment with a variety of triclopy butoxyethyl ester compositions. Another such treatment program consists of the use of a foliar application of an herbicide to control undesired vegetation. This particular method is attractive because it provides not only vegetation control but, when a selective herbicide is used, desirable vegetation is encouraged.

In order to have the herbicide penetrate into the woody plant, it is desirable to dissolve the herbicide in a non-aqueous organic carrier. As currently used, as in Garlon™ 4 herbicide, for example, such carriers consists of petroleum distillates such as fuel oils, e.g., diesel oil or kerosene.

However, these carriers present risks not only to the surrounding environment, but also to the applicator as well. In aerial applications, for example, due to applicator technique or wind conditions, over-spray onto surrounding areas may result in unplanned deposition of the carriers during the application.

SUMMARY OF THE INVENTION

The present invention concerns an herbicidal composition consisting essentially of about 70 to about 95 weight percent triclopy butoxyethyl ester and about 5 to about 30 weight percent of a surfactant. A preferred surfactant comprises a mixture of about 25 to about 65 weight percent of an alkylbenzenesulfonate salt, about 25 to about 45 weight percent of an ethylene oxide-propylene oxide block copolymer and about 15 to about 35 weight percent of an ethoxylated-propoxylated fatty alcohol. Another aspect of the present invention concerns a method for controlling undesired woody vegetation which comprises applying to the foliage or to the basal bark or stem of the woody vegetation an aqueous dilution of the herbicidal composition. In addition to providing for more efficient treatment procedures, i.e., both foliar and basal bark applications, and providing reduced exposure to aromatic carriers, the present composition provides unexpected improved control of a number of key woody plants.

DETAILED DESCRIPTION OF THE INVENTION

This invention provides a solventless herbicidal composition consisting essentially of triclopy butoxyethyl ester and a surfactant.

Triclopyr is the common name for 3,5,6-trichloro-2-pyridinyloxyacetic acid. This compound is a selective systemic herbicide used in the control of brush and woody vegetation, and many broad-leaved weeds, in areas such as grasslands and other uncultivated lands, industrial areas, rights-of-way, coniferous forests and crops including oil palm and rubber plantations and rice.

The butoxyethyl ester of triclopyr is commercially available from Dow AgroSciences as Garlon™ 4 herbicide, a 4 lb acid equivalents/gallon formulation containing petroleum distillates as solvents and carriers for the active ingredient, triclopyr.

The surfactant of the present invention can be anionic, cationic or nonionic in character. Typical surfactants include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; and mixtures thereof.

A preferred surfactant used in the solventless composition of the present invention is a mixture of an alkylbenzene sulfonate salt, a block copolymer of ethylene oxide and propylene oxide and an ethoxylated-propoxylated fatty alcohol.

The alkylbenzene sulfonate salt preferably comprises from about 25 to about 65 and more preferably from about 30 to about 60 weight percent of the surfactant mixture (based on the active substances). Suitable alkylbenzene sulfonate salts include the alkaline earth metal, ammonium, amine, alkanolamine salt of an alkylbenzene sulfonate. Preferably, the alkylbenzene sulfonate comprises an alkyl group containing from about 8 to about 22 carbon atoms. Preferably, the anionic surfactant comprises a calcium or magnesium salt of an alkylbenzene sulfonate and most preferably the calcium salt. The most preferred alkylbenzene sulfonate is the calcium salt of dodecylbenzene sulfonate.

The block copolymer of ethylene oxide and propylene oxide, which may be capped or started at least at one end with an aliphatic, aromatic or cycloaliphatic moiety, comprises from about 25 to about 45 weight percent of the surfactant mixture. Preferably, an ethylene oxide-propylene oxide block copolymer is started with an aryl or aliphatic group which may be cyclic. Block copolymers of ethylene oxide and propylene oxide ranging from about 5 to about 25 ethylene oxide units and from about 20 to about 40 propylene oxide units are suitable with about 10 to about 20 ethylene oxide units and from about 25 to about 35 propylene oxide units being preferred.

The ethoxylated-propoxylated fatty alcohol comprises from about 15 to about 35 weight percent of the surfactant mixture. $C_{10}$-$C_{18}$ Fatty alcohols or mixtures thereof are suitable with $C_{12}$-$C_{14}$ fatty alcohols generally preferred. The fatty alcohols are ethoxylated and propoxylated with ethylene oxide and propylene oxide ranging from about 1 to about 10 ethylene oxide units and from about 1 to about 15 propylene oxide units, with about 1 to about 5 ethylene oxide units and from about 5 to about 10 propylene oxide units being preferred. The ethylene oxide and the propylene oxide units may be block or random.

The compositions of the present invention contain from about 70 to about 95 weight percent of triclopyr butoxyethyl ester and from about 5 to about 30 weight percent of surfactant mixture. Preferably the composition contains from about 80 to about 90 weight percent of triclopyr butoxyethyl ester and from about 10 to about 20 weight percent of surfactant mixture.

In addition to the compositions and uses set forth above, the present invention also embraces the composition and use of these triclopyr butoxyethyl ester compositions in combination with one or more additional compatible ingredients. Other additional ingredients may include, for example, one or more other herbicides, dyes, and any other additional ingredients providing functional utility, such as, for example, stabilizers, fragrants, viscosity-lowering additives, and freeze-point depressants.

Additional herbicidal compounds employed as supplements or additives should not be antagonistic to the activity of the triclopyr butoxyethyl ester composition as employed in the present invention. Suitable herbicidal compounds include, but are not limited to 2,4-D, 2,4-MCPA, ametryn, aminopyralid, asulam, atrazine, butafenacil, carfentrazone-ethyl, chlorflurenol, chlormequat, chlorpropham, chlorsulfuron, chlortoluron, cinosulfuron, clethodim, clopyralid, cyclosulfamuron, DE-742, dicamba, dichlobenil, dichlorprop-P, diclosulam, diflufenican, diflufenzopyr, diuron, fluroxypyr, glyphosate, hexazinone, imazamox, imazapic, imazapyr, imazaquin, imazethapyr, imazosulfinuron, MCPA, metsulfuron-methyl, picloram, pyrithiobac-sodium, sethoxydim, sulfometuron, sulfosate, sulfosulfuron, tebuthiuron, terbacil, thiazopyr, thifensulfuron, triasulfuron and tribenuron.

Particularly useful herbicidal compounds for use with triclopyr butoxyethyl ester in foliar brush-control applications are clopyralid esters and amines, e.g., 3,6dichloro-2-pyridinecarboxylic acid monoethanolamine salt, as well as mixtures with fluroxypyr 1-methylheptyl ester, with aminopyralid salts, with 2,4-D butoxyethyl ester or 2-ethylhexyl ester, and with picloram iso-octyl ester. The herbicidal composition used in the method of the present invention can be formulated with the other herbicide or herbicides, tank mixed with the other herbicide or herbicides, or applied sequentially with the other herbicide or herbicides.

Dyes may be used in the formulated composition as a marker. Generally, a preferred dye can be any oil-soluble dye selected from EPA's approved list of inerts exempt from tolerance. Such dyes, may include, for example, D&C Red #17, D&C Violet #2, and D&C Green #6. Dyes are generally added to the composition by adding the desired amount of dye to the formulated composition with agitation. Dyes are generally present in the final formulation composition in a concentration of about 0.1-1.0% by weight.

The compositions of the present invention are diluted with water prior to being applied to the foliage of the woody vegetation. The diluted compositions usually applied to the woody vegetation generally contain about 0.0001 to about 20.0 weight percent triclopyr butoxyethyl ester.

The following examples illustrate the present invention.

EXAMPLE 1

Preparation of Surfactant Mixture

Agnique™ ABS 60C—dodecylbenzene sulfonate calcium salt (60% active)—(50 g) was warmed to 40° C. While stirring, molten (35° C.) Agnique™ BP NP-1530—nonylphenol block copolymer PO(30) EO(15)—(30 g) and then Dehypon™ LS 36—$C_{12}$-$C_{14}$ fatty alcohol PO(6) EO(3)—(20 g) was added. The mixture was stirred until a single phase was obtained.

EXAMPLE 2

Preparation of Triclopyr Butoxyethyl Ester Formulation

The surfactant mixture from Example 1 (14 g), was added with stirring at room temperature to 86 g of technical triclopyr butoxyethyl ester. Stirring was continued until a single phase was obtained.

EXAMPLE 3

Herbicidal Testing

Trials were conducted at four locations in mixed and single species woody plant sites. Target woody brush was six feet or less and application was conducted over the top with hand held booms. The study was designed to compare the solventless formulation of Example 2 to the commercially available Garlon 4 formulation that contains kerosene. The rates selected were based on the target species. In mixed brush, the rates were 1.5 and 3.0 pounds acid equivalents per acre (lbs ae/ac) (1.68 and 3.36 kilogram acid equivalent per hectare (kg ae/ha)). For Scotch broom the rates were 1.25 lbs ae/ac (1.4 kg ae/ha). The formulations were diluted in water and applied at a delivery volume of 20 gallons per acre (gpa) (187 liters per hectare (L/ha)). No surfactant was added to the mixtures. Sites were treated in the growing season and assessment of control was made the following year. The results (percent control) are summarized in Table I.

TABLE I

| Species Common Name | Solventless Formulation | | Kerosene Garlon 4 | |
| --- | --- | --- | --- | --- |
| | 1.25 lbae/ac (1.4 kgae/ha) Percent control | | 1.25 lbae/ac (1.4 kgae/ha) Percent control | |
| scotch broom | 85 | | 65 | |
| | 1.5 lbae/ac (1.68 kgae/ha) | 3.0 lbae/ac (3.36 kgae/ha) | 1.5 lbae/ac (1.68 kgae/ha) | 3.0 lbae/ac (3.36 kgae/ha) |

TABLE I-continued

| Species Common Name | Solventless Formulation | | Kerosene Garlon 4 | |
|---|---|---|---|---|
| | Percent control | Percent control | Percent control | Percent control |
| sweetgum | 55 | 83 | 43 | 61 |
| cherry | 47 | 57 | 30 | 37 |
| loblolly pine | 13 | 63 | 26 | 40 |
| red oak | 50 | 77 | 47 | 58 |
| water/willow oak | 50 | 77 | 47 | 62 |

What is claimed:

1. An herbicidal composition consisting essentially of about 70 to about 95 weight percent triclopyr butoxyethyl ester and about 5 to about 30 weight percent of a surfactant which comprises a mixture of about 25 to about 65 weight percent of an alkylbenzenesulfonate salt, about 25 to about 45 weight percent of an ethylene oxide-propylene oxide block copolymer and about 15 to about 35 weight percent of an ethoxylated-propoxylated fatty alcohol.

2. A method for controlling undesired woody vegetation which comprises applying to the foliage or to the basal bark or stem of the woody vegetation an aqueous dilution of the herbicidal composition of claim 1.

3. The method of claim 2 in which the herbicidal composition is used with an additional herbicide.

4. The method of claim 3 in which the additional herbicide is aminopyralid, clopyralid, fluroxypyr or picloram.

* * * * *